US00RE35164E

United States Patent [19]

Kindberg et al.

[11] E Patent Number: Re. 35,164

[45] Reissued Date of Patent: Mar. 5, 1996

[54] SURGICAL DEVICE FOR ENCLOSING AN INTERNAL ORGAN

[75] Inventors: Richard C. Kindberg, Doylestown, Pa.; Chao Chen, Edison, N.J.; Lyn Freeman, Flemington, N.J.; Constance E. Roshdy, New Egypt, N.J.; Alastair W. Hunter, Bridgewater, N.J.

[73] Assignee: Ethicon, Inc., Somerville, N.J.

[21] Appl. No.: 97,555

[22] Filed: Jul. 23, 1993

Related U.S. Patent Documents

Reissue of:

[64] Patent No.: 5,143,082
Issued: Sep. 1, 1992
Appl. No.: 679,893
Filed: Apr. 3, 1991

[51] Int. Cl.[6] ..... A61B 10/00

[52] U.S. Cl. ..... 128/749; 128/DIG. 24; 600/37; 606/151

[58] Field of Search ..... 128/749, 849, 128/850, 852, 856, DIG. 24; 606/151, 139, 127, 128; 604/22, 27; 600/37

[56] References Cited

U.S. PATENT DOCUMENTS

| | | |
|---|---|---|
| 2,143,910 | 1/1939 | Didusch . |
| 2,610,631 | 9/1952 | Calicchio . |
| 3,409,014 | 11/1968 | Shannon . |
| 3,476,114 | 11/1969 | Shannon et al. . |
| 3,476,115 | 11/1969 | Graeff et al. . |
| 3,665,926 | 5/1972 | Flores . |
| 3,983,863 | 10/1976 | Janke et al. . |
| 4,177,813 | 12/1979 | Miller et al. . |
| 4,428,375 | 1/1984 | Ellman . |
| 4,578,451 | 3/1986 | Weaver et al. . |
| 4,875,482 | 10/1989 | Hariri et al. . |
| 4,878,890 | 11/1989 | Bilweis . |
| 4,991,593 | 2/1991 | LeVahn . |
| 5,037,379 | 8/1991 | Clayman et al. . |
| 5,041,129 | 8/1991 | Hayhurst . |
| 5,057,117 | 10/1991 | Atweh . |
| 5,129,912 | 7/1992 | Noda et al. . |

OTHER PUBLICATIONS

Davol Rubber Company Catalog, p. 24 (1959).
Ison et al., *J. of Med. Engineering and Technology*, 13(6):285–280 (1989).
General Surgery News, 11(10) (1990).

*Primary Examiner*—Stephen C. Pellegrino
*Assistant Examiner*—Guy V. Tucker
*Attorney, Agent, or Firm*—Dressler, Goldsmith, Shore & Milnamow, Ltd.

[57] ABSTRACT

A medical device for enclosing an internal bodily organ or tissue during surgery comprising a filamentary strand with noose and free end portions, the free end portion enclosed within a cannula; a surgical bag with an opening, the bag attached to the noose portion at the open end of the bag; and a means for pulling the free end portion proximally to reduce the diameter of the noose portion so as to close the open end of the surgical bag.

22 Claims, 5 Drawing Sheets

SURGICAL DEVICE FOR ENCLOSING AN INTERNAL ORGAN

Matter enclosed in heavy brackets [ ] appears in the original patent but forms no part of this reissue specification; matter printed in italics indicates the additions made by reissue.

BACKGROUND OF THE INVENTION

As medical and hospital costs continue to increase. surgeons are constantly staving to develop advanced surgical techniques. Advances in the surgical field are often related to the development of operative techniques which involve less invasive surgical procedures and reduce overall patient trauma. In this manner, the length of hospital stays can be significantly reduced, and therefore the hospital and medical costs can be reduced as well.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a cannula after puncture through the wall of the body cavity with a trocar, which is a sharp-pointed instrument. The surgeon can then perform diagnostic and therapeutic procedures at the surgical site with the aid of specialized instrumentation designed to fit through additional cannulas providing openings into the desired body cavity as may be required.

In many surgical procedures, including those involved in endoscopic surgery, it is often necessary to remove bodily tissue or damaged bodily organs. This is especially challenging during endoscopic surgery because of the small openings through which such tissue or organs must be removed. Under these circumstances, it is necessary to fragment, or morcellate, the bodily tissue so that it can be readily removed through the small endoscopic openings.

In response to the need to morcellate and remove bodily tissue during endoscopic surgery, devices have been developed to aid the surgeon. For example, Ison et al., Journal of Medical Engineering and Technology, Vol. 13, No. 6 (Nov./Dec. 1989), pages 285–289, discloses an endoscopic or laparoscopic instrument for removing tissue, referred to in the an as a tissue morcellator, through a small cross-section. An article in General Surgery News, 11 (10) 1990 illustrales the feasibility of laparoscopic nephrectomy which is an endoscopic procedure for excising a kidney, by first enclosing the desired kidney in a nylon drawstring entrapment sack and then using a tissue morcellator to fragment and aspirate the kidney from the sack.

In other endoscopic surgical procedures, it is often necessary or desired to enclose a fractured organ during surgical repair to aid the surgeon in maintaining the integrity of the bodily organ. A device for accomplishing this task is disclosed in U.S. Pat. No. 4,428,375. This patent describes a drawstring mesh or net bag for encapsulating a fractured organ during surgical repair. The bag is intended to conform to the organ shape and compress the organ sufficiently to close any organ fractures and provide hemostasis. Similar type devices for enclosing fractured or damaged organs are described in U.S. Pat. Nos. 4,878,890; 2,143,910 and 3,983, 863. Unfortunately, none of the devices described in these patents are particularly suitable for endoscopic surgery.

In view of the advances made to date in the field of endoscopic surgery, it would be desirable to fabricate an endoscopic instrument which can perform a variety of functions to enable the surgeon to carry out surgical procedures endoscopically. More specifically, it would be desirable to fabricate an endoscopic device capable of morcellating bodily tissue or organs and to remove such tissue or organs, and to facilitate the surgical repair of fractured organs with an endoscopic device capable of enclosing such fractured organs.

SUMMARY OF THE INVENTION

The invention is a medical device for enclosing an internal bodily organ or tissue during surgery. The device comprises a continuous, filamentary strand having a distal noose portion and a proximal free end portion, said free end portion enclosed within a generally rigid longitudinal tubular sleeve so as to facilitate handling of said device; a surgical bag having an open end therein, said bag fixedly attached along substantially the entire perimeter of said open end thereof to said noose portion of said filamentary strand along substantially the entire circumferential length of said noose portion thereof; and means for pulling said free end portion of said filamentary strand proximally so as to continually reduce the diameter of said noose portion thereby continually closing said open end of said surgical bag.

The medical device of this invention is particularly adapted for use during endoscopic surgical techniques. The device can be used during any operative procedure requiring the enclosure of bodily tissue or bodily organs.

DETAILED DESCRIPTION OF THE PREFERRED EMBODIMENTS

As defined in this application, the word "distal" is used to describe that portion of the device which extends away from the user during use, and the word "proximal" is used to describe that portion of the device that extends toward the user during use.

Figures 1, 2:
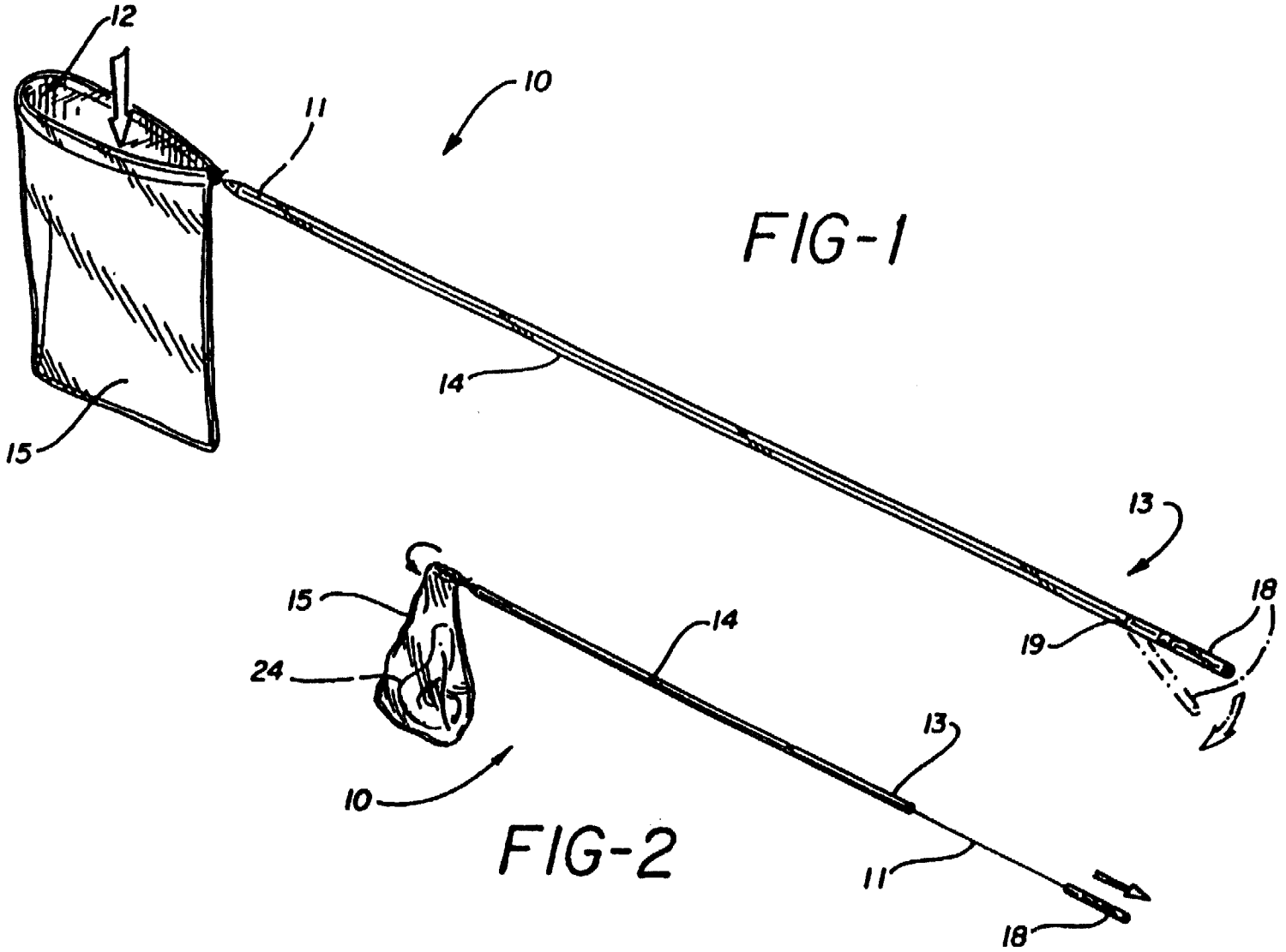
FIG. 1 is a perspective view of the medical device of this invention.
FIG. 2 is a perspective view of the medical device on a reduced scale after the device is used to enclose a bodily organ.

Referring to the Figures, FIG. 1 illustrates a medical device at 10 representing a preferred embodiment of this invention. The device includes a continuous filamentary strand 11 having a distal noose portion 12 and a Proximal free end portion 13. Strand 11 can be Prepared from any conventional surgical suture material, e.g. nylon, silk, steel, catgut, and conventional bioabsorbable suture materials such as polymers and copolymers of lactide, glycolide, para-dioxanone and trimethylene carbonate. Surgical bag 15 having an opening therein for placement of bodily tissue is attached to distal noose portion 12 along substantially the entire perimeter of the open end of the bag by engagement with substantially the entire length of distal noose portion 12. The free end portion 13 of continuous filamentary strand 11 is enclosed within a generally rigid, longitudinal tubular sleeve 14, often referred to in this an as a cannula. Tubular sleeve 14 has a frangible portion 18 at its proximal end and a score line 19 disposed at the distal end of the frangible portion 18. Continuous filamentary strand 11 is adhesively attached within the frangible portion 18 of the tubular sleeve 14 with a conventional adhesive, e.g. epoxy.

Figure 3:
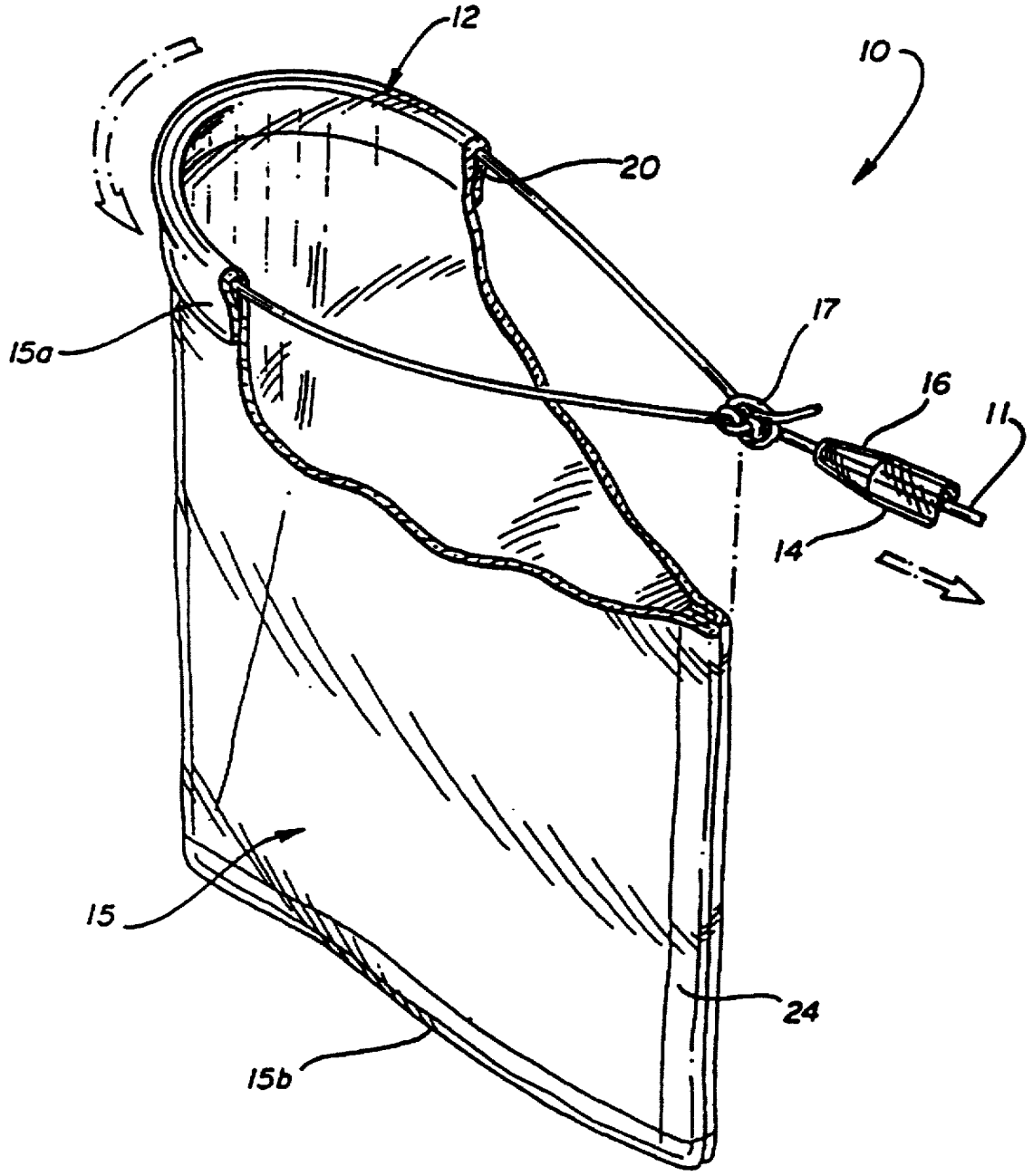
FIG. 3 is an enlarged perspective view of the medical device with a portion of said device broken away.

As illustrated in more detail at FIG. 3, the noose portion 12 of continuous filamentary strand 11 is sealingly engaged within a channel 20 running along the circumferential length of the open end of the surgical bag 15. In this embodiment, channel 20 is formed by folding the top portion of the bag over about itself and sealed along a lower portion of bag 15 to create a top flap portion 15a. In like manner, bag 15 can also have a peripheral edge seal 24 having a closed bottom portion 15b if a hermetic seal is required for the particular surgical application. Still referring to FIG. 3, the noose portion 12 of continuous filamentary strand 11 is secured with a slip knot 17, which allows movement of the free end portion 13 of the continuous filamentary strand 11 proximally and prevents the noose portion 12 from loosening when engaged about bodily tissue. Longitudinal tubular sleeve 14 has a tapered distal end 16 which prevents slip knot 17 from passing through tubular sleeve 14 during use.

Surgical bag 15 can be constructed of a wide variety of materials, but generally the bag used should be biocompatible and non-toxic to bodily tissue and should exhibit the requisite conformability so that it can readily fit down a trocar. If the medical device is to be used to morcellate and remove bodily tissue, then the bag is desirably waterproof to prevent fragmented tissue from escaping the bag. Additionally, for this application, the bag should have a high tear and burst resistance, a low modulus and moderate elongation. Although a variety of materials can be used for this purpose, the preferred material of construction for the surgical bag for this application is PEBAX™ block copolyetheramide. Alternatively, if the bag is to be used for encapsulating a fractured organ during surgical repair, then it may be desirable to employ a bag which has a mesh network. See, for example, U.S. Pat. No. 4,428,375, which describes a variety of pliable surgical materials well known in the art for this application that can be fabricated into a desired mesh structure.

Referring now to FIGS. 1 and 2 in combination, one can see generally how the device is used to enclose bodily tissue. In order to encapsulate bodily organ 24, as seen in FIG. 2, the user would first grip frangible portion 18 of tubular sleeve 14 with one hand and the remaining portion of tubular sleeve 14 with the other hand, and then snap apart the two pieces about score line 19. This allows for the continuous filamentary strand 11 to be retracted through the longitudinal tubular sleeve 14 as shown in FIG. 2. Following this simple procedure, the user could then place the surgical bag 15 about a desired bodily organ 24, positioning the bag at the appropriate location about bodily organ 24. To complete the procedure, continuous filamentary strand 11 is pulled proximally as shown by the arrow at FIG. 2, causing the distal noose portion 12 of strand 11 to close the open end of surgical bag 15. As shown more clearly at FIG. 3, knot 17 is restrained by tapered end 16 of the longitudinal tubular sleeve 14 while the user is pulling strand 11 proximally and allows strand 11 to pass through the tubular sleeve 14 so that the distal noose portion 12 may be closed about bodily organ 24. The knot configuration must be such that once the distal noose portion 12 is closed about bodily organ 24, it remains closed and does not loosen.

Figure 4:
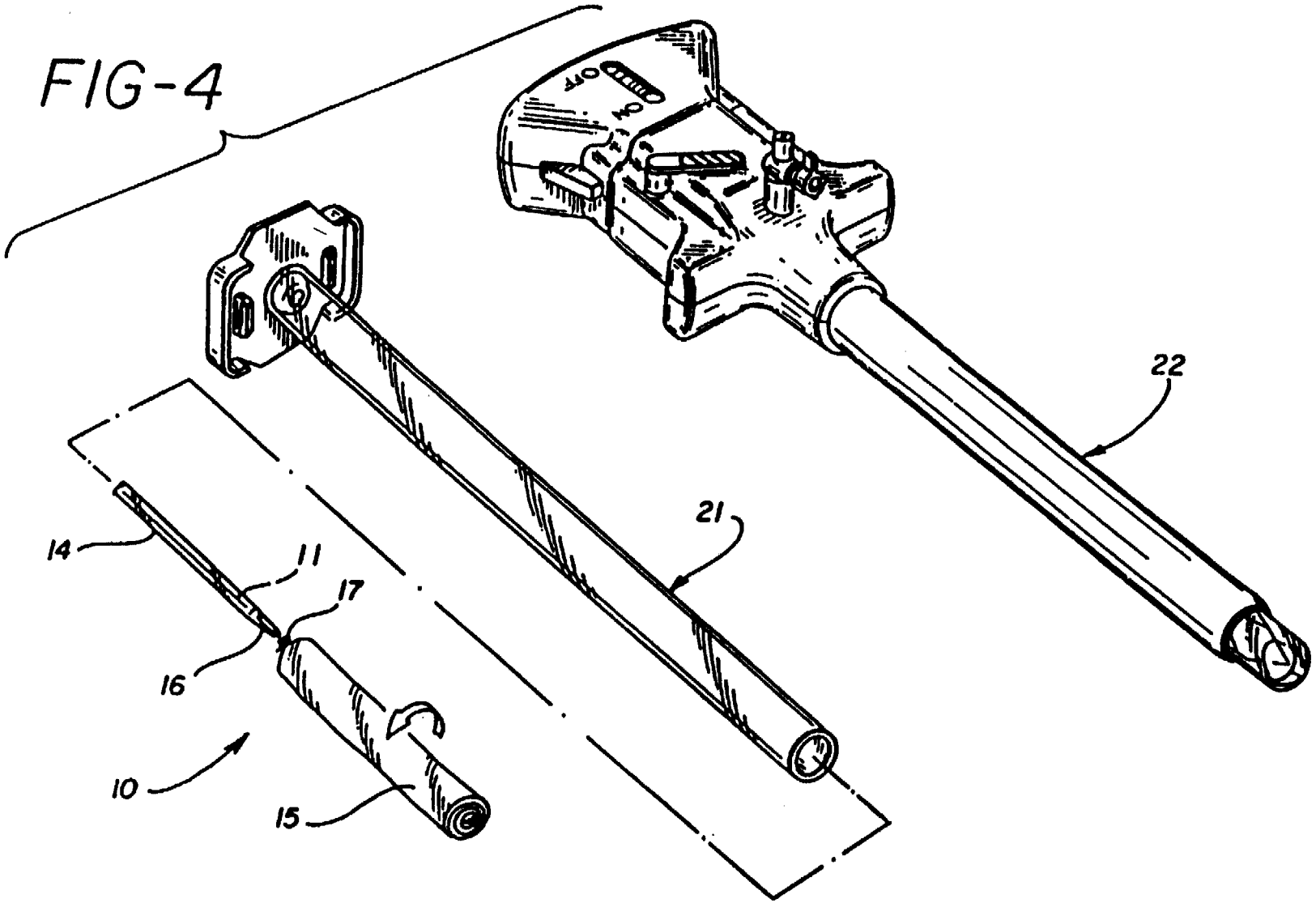
FIG. 4 is an exploded perspective view of the medical device of this invention in combination with conventional endoscopic instruments to facilitate the use of the device during endoscopic surgery.
Figure 5:
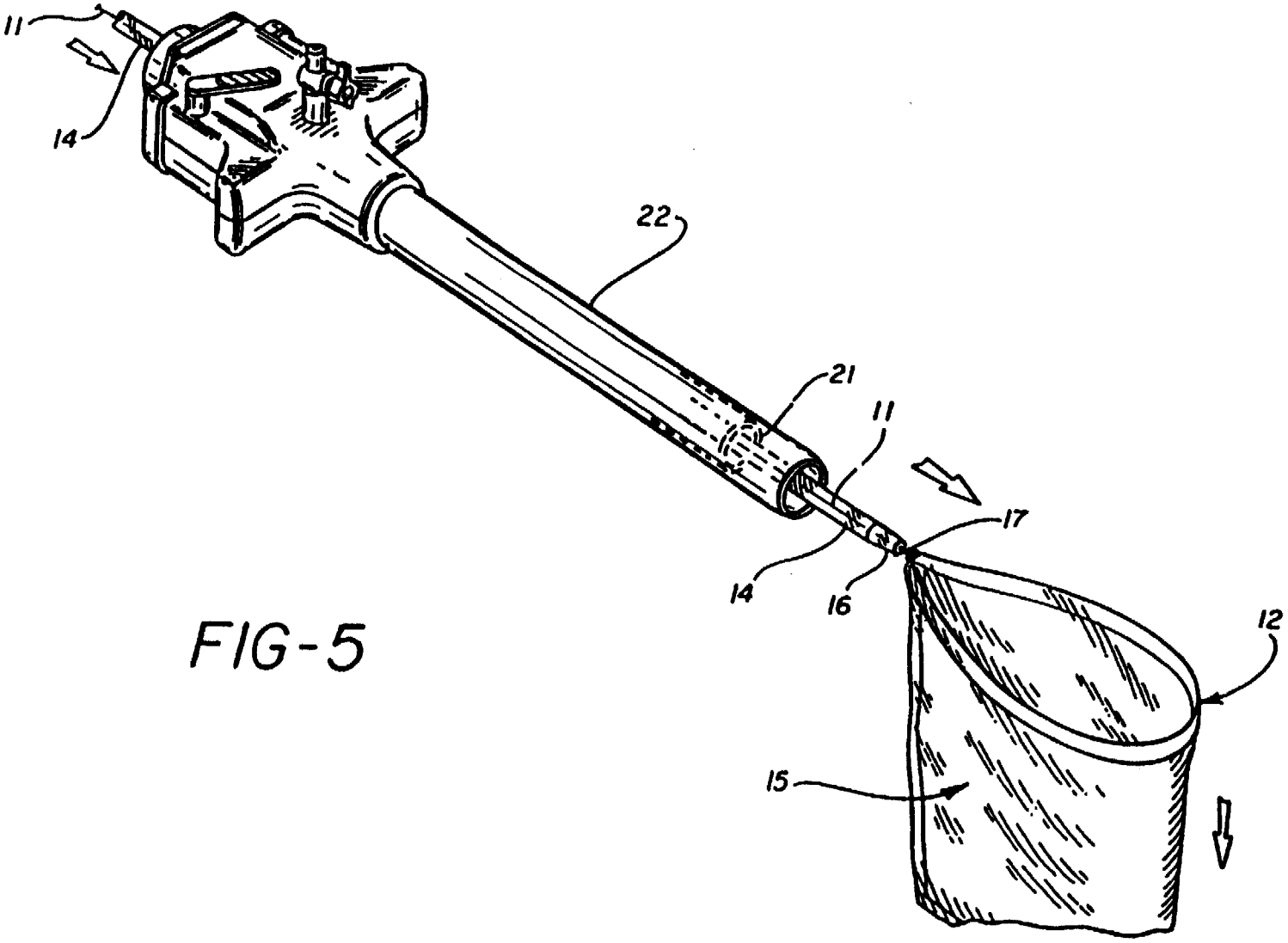
FIG. 5 is a perspective view illustrating the operation of the medical device of this invention.
Figure 6:
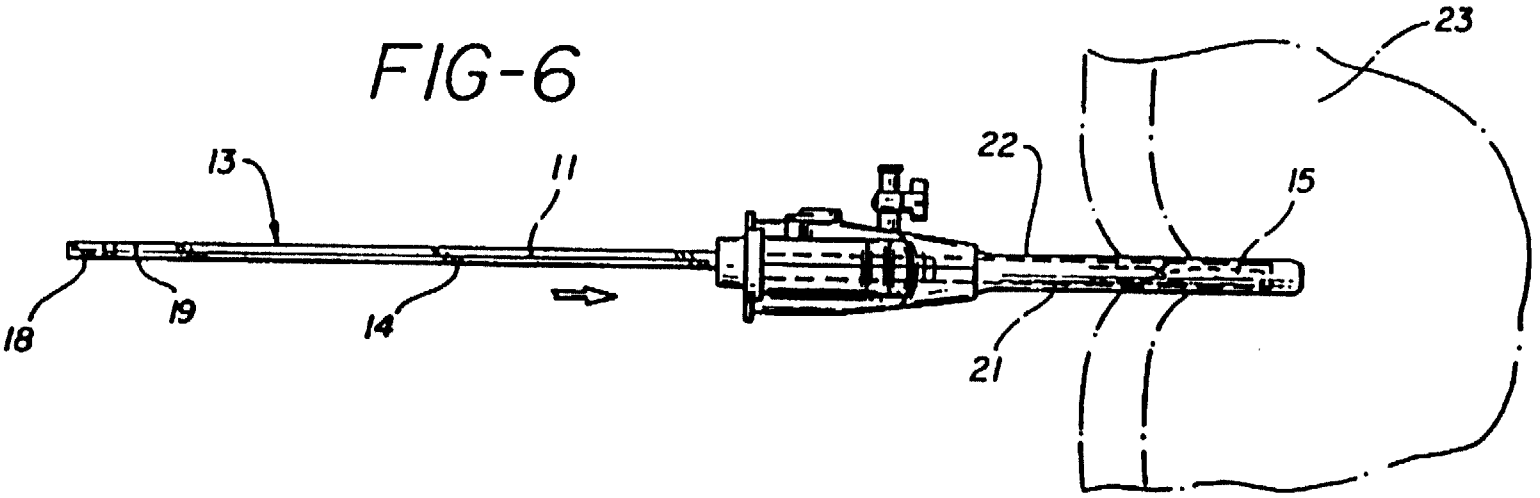
FIGS. 6 and 7 are perspective views illustrating the operation of the medical device of this invention within bodily tissue.
Figure 7:
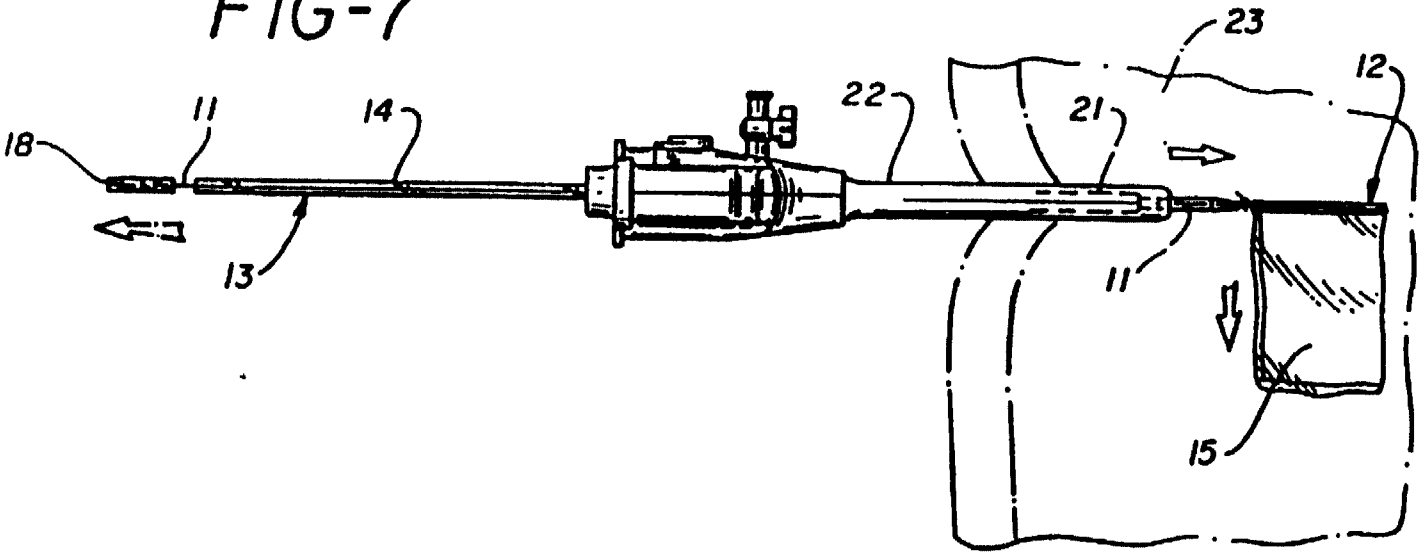

Referring now to FIG. 4, the medical device of this invention can be used in combination with introducer 21 and trocar 22 to facilitate its use during endoscopic surgery. First, the surgical bag 15 is folded about the axis of the proximal free end portion 13 of continuous filamentary strand 11 so as to facilitate the insertion of the medical device into introducer 21. After the medical device is inserted into introducer 21, the introducer can then be placed within an appropriately sized trocar 22 for insertion into the desired bodily cavity. As shown in FIGS. 5–7, the trocar 22 is introduced into a desired bodily cavity until penetration of the desired bodily tissue 23. As shown in FIG. 7, once the trocar is appropriately placed, the medical device of this invention can be moved distally through introducer 21 and trocar 22 so as to cause surgical bag 15 to protrude from introducer 21 and into bodily tissue 23. Once bag 15 is placed within desired bodily tissue 23 free of the confines of the reducer and trocar, it can unfold as shown by the arrows at FIGS. 5 and 7. After surgical bag 15 unfolds, the user can then manipulate the device so as to place unfolded surgical bag 15 about a desired bodily tissue, and then the user can perform the procedure outlined above to carry out the required operation.

Following the surgical operation, the bag 15 can either be removed from the surgical site or be left intact at the site, depending on the operative procedure performed. For example, if bodily tissue is morcellated within the bag 15, and therefore it becomes necessary to remove the fragmented tissue from the body, then the bag 15 can be readily removed by pulling the tubular sleeve 14 proximally through introducer 21 and trocar 22 until the entire medical device 10, including bag has been removed from the body. Alternatively, if bag 15 is composed of a bioabsorbable surgical mesh, and the bag 15 is used to facilitate the repair of a damaged organ over an extended period of time, it may be desirable to leave bag 15 intact at the surgical site. This can be accomplished simply by first cutting strand 11 at or near the junction of distal noose portion 12 and free end portion 13, and then pulling tubular sleeve 14 proximally so as to remove the free end portion 13 of strand 11 from introducer 21 and trocar 22 while leaving bag 15 intact within the body.

Although only the most preferred surgical device of this invention is described herein, numerous additional embodiments will become apparent to those skilled in this art, all of which are well within the scope and spirit of the claimed invention.

We claim:

1. A medical device for enclosing an internal bodily organ or tissue during surgery comprising:

a) a continuous, filamentary strand having a distal noose portion secured with a knot, and a proximal free end portion, said free end portion enclosed within a generally rigid, longitudinal tubular sleeve so as to facilitate handling of said device, said knot configured in a manner so as to allow movement of the free end portion proximally and to prevent the noose portion from loosening when engaged about said bodily organ or tissue;

b) a surgical bag having an open end therein, said bag fixedly attached along substantially the entire perimeter of said open end thereof to said noose portion of said filamentary strand along substantially the entire circumferential length of said noose portion thereof; and c) means for pulling said free end portion of said filamentary strand proximally so as to continually reduce the diameter of said noose portion thereby continually closing said open end of said surgical bag;

wherein said tubular sleeve is tapered at its distal end, and said knot abuts said tapered distal end when said free end portion of said filamentary strand is pulled proximally, and said tapered distal end has a cross-section diameter effective to prevent said knot from passing through said tubular sleeve when said free end portion of said filamentary strand is pulled proximally.

2. The medical device of claim 1 wherein said tubular sleeve has a frangible portion at its proximal end.

3. The medical device of claim 2 wherein a score line is disposed at the distal end of said frangible portion.

4. The medical device of claim 3 wherein said free end portion of said filamentary strand is securingly attached within said frangible portion of said tubular sleeve, whereby a user of said medical device can break said tubular sleeve about said frangible portion at said score line and pull proximally said frangible portion so as to pull said free end portion of said filamentary strand proximally.

5. The medical device of claim 4 wherein said free end portion is adhesively attached within said frangible portion with epoxy adhesive.

6. The medical device of claim 5 wherein said bag is composed of block copolyetheramide.

7. The medical device of claim 6 wherein said open end of said bag is securingly engaged to said noose portion of said filamentary strand within a channel disposed along substantially the entire circumferential length of said noose portion, said channel formed by folding said bag about itself at said open end so as to create a top flap portion.

8. The medical device of claim 7 wherein said bag further comprises a closed bottom portion sealed by a peripheral edge seal.

*9. A medical device for enclosing an internal bodily organ or tissue during surgery comprising:*

*a) a continuous, filamentary strand having a distal noose portion secured with a knot, and a proximal free end portion, said free end portion enclosed within a generally rigid, longitudinal tubular sleeve so as to facilitate handling of said device, said knot configured in a manner so as to allow movement of the free end portion proximally and to prevent the noose portion from loosening when engaged about said bodily organ or tissue;*

*b) a surgical bag having an open end therein, said bag fixedly attached along substantially the entire perimeter of said open end thereof to said noose portion of said filamentary strand along substantially the entire circumferential length of said noose portion thereof; and*

*c) means for pulling said free end portion of said filamentary strand proximally so as to continually reduce the diameter of said noose portion thereby continually closing said open end of said surgical bag;*

*wherein said tubular sleeve has a constricted cross-section diameter at its distal end, and said knot abuts said constricted distal end when said free end portion of said filamentary strand is pulled proximally, and said constricted distal end has a cross-section diameter effective to prevent said knot from passing through said tubular sleeve when said free end portion of said filamentary strand is pulled proximally.*

*10. The medical device of claim 9 wherein said tubular sleeve has a frangible portion at its proximal end.*

*11. The medical device of claim 10 wherein a score line is disposed at the distal end of said frangible portion.*

*12. The medical device of claim 11 wherein said free end portion of said filamentary strand is securingly attached within said frangible portion of said tubular sleeve, whereby a user of said medical device can break said tubular sleeve about said frangible portion at said score line and pull proximally said frangible portion so as to pull said free end portion of said filamentary strand proximally.*

*13. The medical device of claim 12 wherein said free end portion is adhesively attached within said frangible portion with epoxy adhesive.*

*14. The medical device of claim 13 wherein said bag is composed of block copolyetheramide.*

*15. The medical device of claim 14 wherein said open end of said bag is securingly engaged to said noose portion of said filamentary strand within a channel disposed along substantially the entire circumferential length of said noose portion, said channel formed by folding said bag about itself at said open end so as to create a top flap portion.*

*16. The medical device of claim 15 wherein said bag further comprises a closed bottom portion sealed by a peripheral edge seal.*

*17. The medical device of claim 9 wherein said tubular sleeve is tapered at its distal end.*

*18. A medical device for enclosing an internal bodily organ or tissue during surgery comprising:*

*a) a continuous, filamentary strand having a distal noose portion secured with a knot, and a proximal free end portion, said free end portion enclosed within a generally rigid, longitudinal tubular sleeve so as to facilitate handling of said device, said knot configured in a manner so as to allow movement of the free end portion proximally and to prevent the noose portion from loosening when engaged about said bodily organ or tissue;*

*b) a surgical bag having an open end therein, said bag fixedly attached along substantially the entire perimeter of said open end thereof to said noose portion of said filamentary strand along substantially the entire circumferential length of said noose portion thereof;*

*c) a grasping member for pulling said free end portion of said filamentary strand proximally so as to continually reduce the diameter of said noose portion thereby continually closing said open end of said surgical bag; and*

*d)* means releasably attaching the grasping member to said tubular sleeve,

*wherein said tubular sleeve has a constricted cross-section diameter at its distal end, and*

*said knot abuts said constricted distal end when said free end portion of said filamentary strand is pulled proximally, and*

*said constricted distal end has a cross-section diameter effective to prevent said knot from passing through said tubular sleeve when said free end portion of said filamentary strand is pulled proximally.*

*19. The medical device of claim 18 wherein said tubular sleeve is tapered at its distal end.*

*20. An endoscopic surgical procedure for enclosing body tissue comprising the steps of:*

*forming an opening establishing a passageway into a body cavity;*

*inserting an open mouth surgical bag into said body cavity by providing the bag at the distal end of a tubular sleeve, and moving said tubular sleeve along said*

*passageway until said distal end of said sleeve and said bag extend outwardly of said passageway;*

*providing a filamentary strand within said tubular sleeve and extending outwardly from the distal end of said tubular sleeve through an opening in a stop surface at the distal end of said tubular sleeve, said filamentary strand having (a) a knot at the distal end thereof, (b) a noose portion engaging the open mouth of said surgical bag and extending from said knot, and (c) a proximal end portion accessible at the proximal end of said tubular sleeve;*

*manipulating the proximal end of said tubular sleeve to (a) locate said open mouth of said surgical bag in alignment with said body tissue, and (b) enclose said body tissue within said surgical bag;*

*and closing the open mouth of said surgical bag by moving said filamentary strand proximally of said tubular sleeve to (a) move said knot into engagement with said stop surface, and (b) tighten said noose, thereby enclosing said body tissue in said surgical bag.*

*21. An endoscopic surgical procedure for enclosing body tissue comprising the steps of:*

*forming an opening establishing a passageway into a body cavity;*

*inserting an open mouth surgical bag into said body cavity by providing the bag at the distal end of a tubular sleeve, and moving said tubular sleeve along said passageway until said distal end of said sleeve and said bag extend outwardly of said passageway;*

*providing a filamentary strand with a noose portion secured by slip knot means, the noose portion engaging the open mouth of said surgical bag, said filamentary strand extending within said tubular sleeve and being accessible at the proximal end thereof;*

*manipulating the proximal end of said tubular sleeve to (a) locate said open mouth of said surgical bag in alignment with said body tissue, and (b) enclose said body tissue within said surgical bag;*

*and closing the open mouth of said surgical bag by moving said filamentary strand proximally of said tubular sleeve so that said tubular sleeve restrains said slip knot means to tighten said noose and thereby enclose said body tissue in said surgical bag.*

*22. An endoscopic surgical procedure for enclosing body tissue comprising the steps of:*

*forming an opening establishing a passageway into a body cavity;*

*inserting an open mouth surgical bag into said body cavity by providing the bag at the distal end of a tubular sleeve, and moving said tubular sleeve along said passageway until said distal end of said sleeve and said bag extend outwardly of said passageway;*

*providing a bag closing means including a noose portion secured by slip knot means, the noose portion engaging the open mouth of said surgical bag, and an actuator for said bag closing means within said tubular sleeve and accessible at the proximal end thereof;*

*manipulating the proximal end of said tubular sleeve to (a) locate said open mouth of said surgical bag in alignment with said body tissue; and (b) enclose said body tissue within said surgical bag;*

*and closing the open mouth of said surgical bag by said actuator so that said tubular sleeve restrains said slip knot means to thereby enclose said body tissue.*

* * * * *